US007036388B1

(12) United States Patent
Genovese et al.

(10) Patent No.: US 7,036,388 B1
(45) Date of Patent: May 2, 2006

(54) SAMPLE HEATER ASSEMBLY AND METHOD OF USE THEREOF

(75) Inventors: James A. Genovese, Street, MD (US); Mark S. DiBeradino, Baltimore, MD (US); Lester D. Strauch, Bel Air, MD (US); Mark S. Schlein, Abingdon, MD (US); Emory W. Sarver, Havre de Grace, MD (US); Arthur Stuempfle, Edgewood, MD (US); Dennis J. Reutter, Churchville, MD (US); Richard S. Simak, Edgewood, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 122 days.

(21) Appl. No.: 10/633,773

(22) Filed: Aug. 4, 2003

Related U.S. Application Data

(60) Provisional application No. 60/407,358, filed on Aug. 29, 2002.

(51) Int. Cl.
*G01N 33/00* (2006.01)
*G01N 1/44* (2006.01)

(52) U.S. Cl. .................... 73/863.12; 73/64.56; 73/866; 436/181

(58) Field of Classification Search ............................... 73/863.11–863.12, 863.23, 31.07, 64.56, 73/866; 422/61, 68.1, 80; 436/147, 177, 436/181
See application file for complete search history.

(56) References Cited

U.S. PATENT DOCUMENTS

| | | | | |
|---|---|---|---|---|
| 4,048,022 | A * | 9/1977 | Epstein et al. | 205/785.5 |
| 4,433,982 | A * | 2/1984 | Odernheimer et al. | 96/4 |
| 4,542,641 | A * | 9/1985 | Eyler | 73/863.12 X |
| 5,345,809 | A * | 9/1994 | Corrigan et al. | 73/863.12 X |
| 6,125,687 | A * | 10/2000 | McClelland et al. | 73/863.12 X |
| 6,174,732 | B1 * | 1/2001 | Ong et al. | 436/177 |
| 6,228,657 | B1 * | 5/2001 | Genovese et al. | 422/61 X |
| 6,295,860 | B1 * | 10/2001 | Sakairi et al. | |
| 2003/0230152 | A1 * | 12/2003 | McGill et at | 73/863.12 X |

* cited by examiner

*Primary Examiner*—Thomas P. Noland
(74) *Attorney, Agent, or Firm*—Ulysses John Biffoni

(57) ABSTRACT

A sample heater assembly which permits the detection of low volatility agents by existing chemical agent detectors is described. Existing chemical agent detectors often lack the capability to accurately detect low volatility agents, such as the chemical warfare agent VX. The sample heater assembly provides this capability by heating low volatility agents to vaporization and interfacing with the existing chemical agent detector. The sample heater assembly comprises a sample containment reservoir for holding the low volatility agent sample, which can be attached to the chemical agent detector, and a heating element which attaches to the sample containment reservoir for heating the sample.

18 Claims, 3 Drawing Sheets

SAMPLE HEATER ASSEMBLY AND METHOD OF USE THEREOF

CROSS-REFERENCE TO RELATED APPLICATIONS

This application claims the benefit of priority from U.S. Provisional Patent Application Ser. No. 60/407,358, filed on Aug. 29, 2002.

GOVERNMENT INTEREST

The invention described herein may be manufactured, licensed, and used by or for the U.S. Government.

BACKGROUND OF THE INVENTION

1. Field of the Invention

The present invention provides a sample heater assembly that provides an enhanced ability to detect low volatility agents, such as particular chemical warfare agents.

2. Brief Description of the Related Art

Low volatility agents (LVA), particularly in the chemical warfare agent nerve agent class of VX, pose a very toxic and persistent hazard to conventional military forces and possibly to civilian populations. Commonly known as a weapons of mass destruction (WMD), these chemical warfare agents are potentially employed as a tactical or terror weapon in various military scenarios, such as being deployed in military actions for effective terrain denial using a variety of dissemination mechanisms including grenades, mortars, mines, rockets, bombs and long-range projectiles and missiles. Likewise, terrorists employing these or other dispersal devices could also disperse these hazardous compounds. Although these low volatility agent hazards normally produce minimal vapor inhalation hazard, if properly configured, high explosive mechanisms and special configuration sprayers can produce airborne droplets and aerosols in addition to significant liquid ground deposition contamination. In such forms, these hazards are generally liquids and exhibit physical/chemical properties quite different from respiratory hazard chemical warfare agents (CWAs), e.g. Sarin (GB). Low vapor pressure hazards, such as low volatility agents, are difficult to detect using currently known fielded vapor detectors.

These low volatility agents, because of their low vapor pressures, are difficult to detect with the current chemical vapor detection systems such as the Improved Chemical Agent Monitor (ICAM) and the M256A1 Chemical Agent Detector Kit. The M256 detector Kit, for example, detects Sarin (GB) to a sensitivity level of 0.005 mg-min/m$^3$ using a very specific eel enzyme cholinesterase. This enzyme is similar to human acetyl cholinesterase and its activity is reduced with exposure to organophosphorus hazards, such as Sarin (GB) or VX. As Sarin is approximately 2000 times more volatile than VX, to accomplish VX binding in the vapor state to the eel enzyme cholinesterase in the M256 Chemical Detector Kit, more vapor molecules are necessary to effect detection. The M256A1 Chemical Agent Detection Kit, including its pertinent M256 Chemical Agent Detector, is described in Department of the Army Technical Manual, TM 3-6665-307-10, titled A Operator=s Manual for Chemical Agent Detector Kit, M256 (6665-01-016-8399) and M256A1 (6665-01-133-4964)@, September 1985, which also describes the Mustard Agent Heater Assembly (MAHA) of the M256A1 Chemical Agent Detection Kit. Additionally, the Improved Chemical Agent Monitor (ICAM) is described in Army Technical Manual TM 3-6665-331-10, and the M8 Chemical Agent Detection Paper is described in army supply Bulletin SB 3-6665-2. The disclosure of each of these references for the M256A1 Chemical Agent Detection Kit, M256 Chemical Agent Detector, Mustard Agent Heater Assembly, Improved Chemical Agent Monitor, and M8 Chemical Agent Detection Paper are incorporated herein by reference in their entirety.

As the threat of these chemical warfare agents being used exists, and the proliferation of such chemical weapons continues, there is a need in the art to develop improved methods to detect and sample these hazards. The present invention addresses this and other needs.

SUMMARY OF THE INVENTION

The present invention includes a sample heater assembly, preferably for use with a M256 Chemical Agent Detector, having a heating element and a sample containment reservoir conductively attached thermally to the heating element to effectively vaporize one or more low volatility agents for detection thereof. The sample heater assembly of the present invention advantageously enables detection of low volatility hazardous contaminants in a simple manner by modifying existing equipment. After the hazardous contaminants are placed in the sample containment reservoir, the heating element heats the low volatility hazardous contaminants at effective heating rates that are variable, in part, by adjusting the distance between the heating element and low volatility hazardous contaminants. Heating rates additionally vary with the number and timing of using individual heat sources within the heating element. The heated low volatility hazardous contaminants are kept isolated in the space between the sample containment reservoir and the detection window, with selection of the appropriate detection window generally determined from known or generated intelligence information.

The present invention also includes a M256 Chemical Detector in combination with the sample heater assembly.

Additionally, the present invention includes a method for detecting low volatility agents comprising the steps of providing a sample heater assembly having a heating element and a sample containment reservoir conductively attached thermally to the heating element to effectively vaporize one or more low volatility agents for detection thereof, placing one or more low volatility agents into the sample containment reservoir and heating the sample containment reservoir effectively to vaporize the low volatility agents for detection. A detection paper, such as M8 paper, may be used to initially detect a liquid chemical warfare agent. This wetted detector paper when indication is positive can be inserted into the sample heater assembly with the liquid hazard directly vaporized from the M8 paper. As such the M8 paper serves a dual role as an initial liquid hazard detector, and also serves immediately as a sampling swatch to be inserted into the sample heater assembly for vapor detection with the M256 Detector Kit. A detected chemical warfare agent product results from the method.

Furthermore, the present invention includes an improved M256 Chemical Detection kit that incorporates the sample heater assembly.

DETAILED DESCRIPTION OF THE PREFERRED EMBODIMENT

Figure 1:
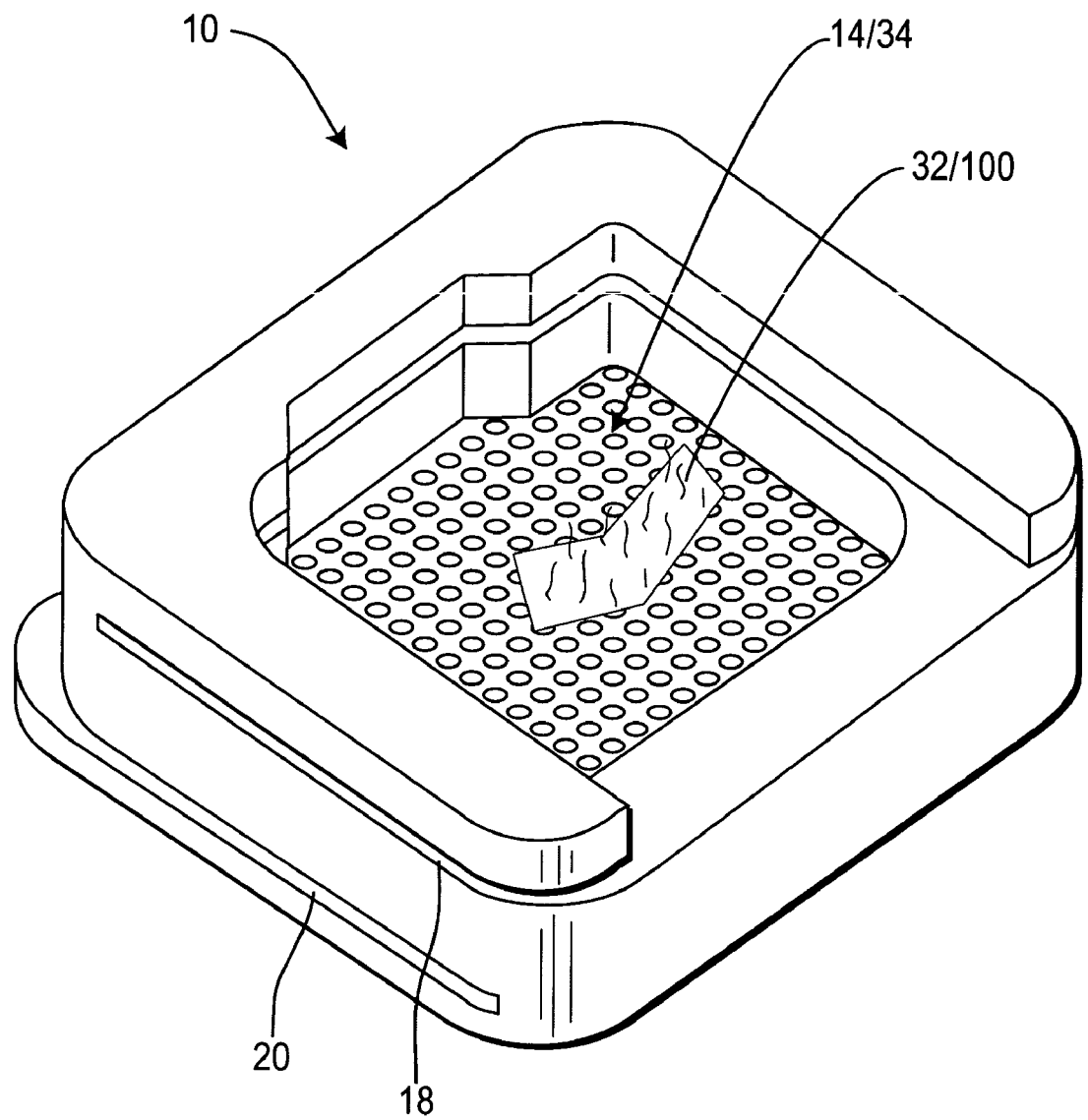
FIG. 1 illustrates the sample heater assembly of the present invention.

The present invention provides for a novel sample heater assembly (SHA) useful in field-expedient sampling and detection of low volatility agents, also known as low volatility hazards (LVH), particularly when employed as part of currently fielded chemical vapor detection instruments, such as an improved M256 Chemical Agent Detection Kit, that is integrated with the sample heater assembly. Many fielded vapor detection instruments do not have the capability to perform detection of especially low volatility samples, and the combination of the sample heater assembly as an adjunct to the existing M256 detection kit affords an expanded and needed detection capability through this combined system. The sample heater assembly, method of and product thereby, enhance the detection capabilities of the currently fielded M256 Chemical Agent Detector Kit through use of the novel sample heater assembly, as taught herein. With the addition of the sample heater assembly, this heater/sample component allows low volatility hazardous liquids to be detected in a field environment particularly in a chemical warfare scenario. As the M256 kit was initially developed to detect a variety of chemical warfare agent vapors or gases, detection of low volatility hazards is problematic for the M256 kit because of the low vapor pressures of these low volatility hazards. The use of the sample heater assembly with the M256 allows detection of chemical composition not previously detectable by the M256 kit. Additionally, the present invention may be used to enhance the detection of low volatility agents using the Improved Chemical Agent Monitor (ICAM). One preferred embodiment of the present invention includes a M256 Chemical Detector in combination with the sample heater assembly. The enhancement of the standard M256 Chemical Agent Detector Kit, as taught herein, to include low volatility liquid sampling and detection imparts a major product improvement that facilitates the detection of a wider range of hazardous chemicals in both battlefield and civilian environments. In addition, the present invention includes the effective and unique integration of the currently fielded M256 Chemical Agent Detector Kit and the M8 Chemical Agent Detector Paper, which constitutes another preferred embodiment of the sampling and detection system of the present invention.

As used herein, the terms low volatility hazards (LVH) and low volatility agents (LVA) are used interchangeably. Although the two terms, low volatility hazards and low volatility agents, are technically distinct including where low volatility agents are the conventional military hazards, the low vapor pressure (or low volatility) of these two types of samples result from the physical/chemical properties of these chemicals, or a combination of the particular chemical sample and the environmental sample matrix in which it is contained. Low volatility agents include chemical warfare agents, such as blister agents, blood agents and nerve agents, including VX. Vapor pressure, usually measured in mm Hg or pascal in SI units, denotes the tendency of liquids to vaporize. Volatility, however, is a quantitative term that includes molecular considerations and is used to describe the concentration of a vapor above a liquid under equilibrium conditions in a closed system at a specific temperature (usually measured in $mg/m^3$). Additionally, meteorological conditions impart significant influence on how easily these low volatility liquids are detected, for example colder environments tend to lower the vapor pressure of these hazards.

Figure 3:
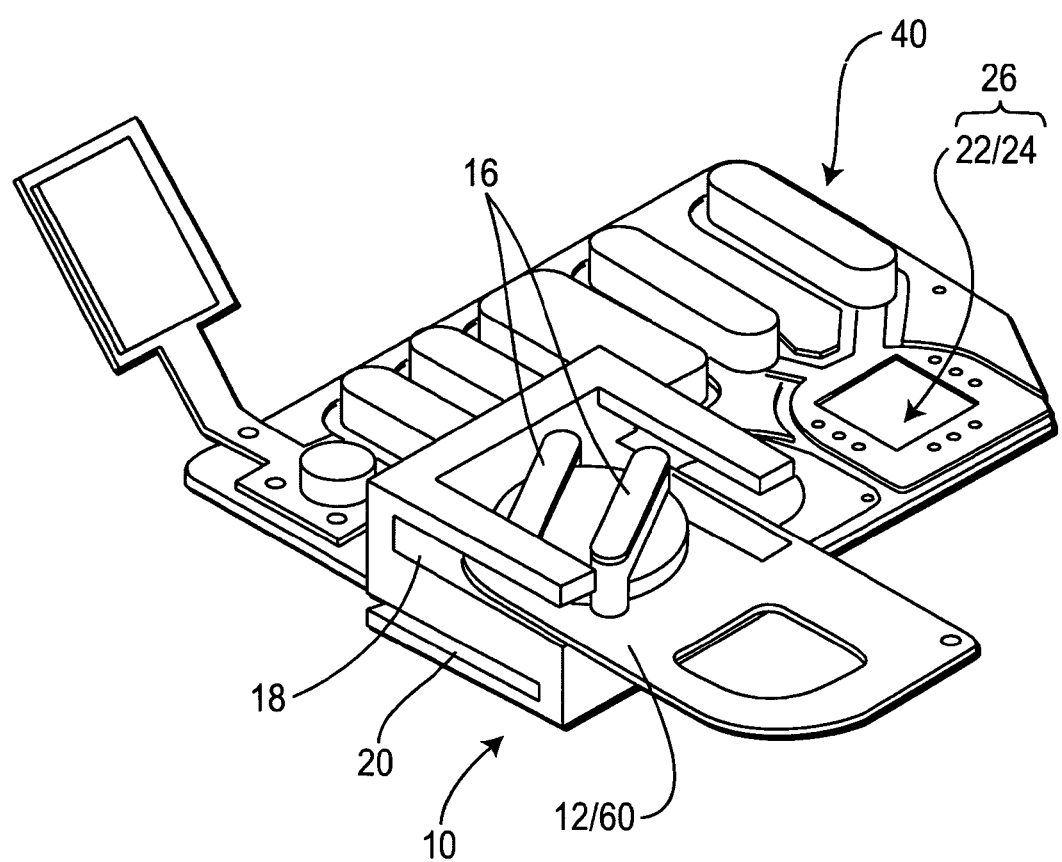

As seen in FIGS. 1 and 3, the present invention expands the field detection capability of the M256 Kit with the use of a sample heater assembly 10. The sample heater assembly 10, shown individually in FIG. 1 and in combination with other components in FIG. 3, increases the effective vapor pressure of low volatility hazardous liquids, particularly chemical warfare agents such as VX. The combination of the sample heater assembly 10 and an M256 detector 40 (shown in FIG. 3) provides the M256 with expanded capability to detect additional chemical warfare agent, such as VX, or mustard agent, such as HD. The sample heater assembly 10 of the present invention includes a heating element 12 and a sample containment reservoir 14, with the sample containment reservoir 14 conductively attached thermally to the heating element 12 in a manner to effectively vaporize one or more low volatility agents for detection of the low volatility agents thereof.

In a preferred embodiment the sample heater assembly 10 includes a small, lightweight structure constructed of materials that are not degraded by the thermal heating or by the chemical sample being vaporized and detected. Such materials include stainless steel, hardened polymeric compositions, plastic polymers, metals, metal alloys, composites and the like, with selection of the appropriate material determinable by those skilled in the art through ordinary experimentation in light of the disclosure herein, including considerations of interfering chemical breakdown products or other interferents generated from either the thermal heating process, or interactions with the chemical samples themselves, thus interfering with the resultant vapor detection on the M256 detector 40. Variations and subsequent changes to the sample containment reservoir 14, or the sample heater assembly 10, may include optimized designs, or redesigns, for production and marketing, such as for example without limitation, changes in the size or geometry of the sample compartment reservoir 14 or the sample heater assembly 10 to enhance performance, production rates, compatibility, convenience, etc., with designs, adjustment or changes preferably completed to maximize diffusion of the heated low volatility sample vapors to afford a more rapid time period and/or accurate detection by the detector, generally by optimizing sample diffusion after heating and detection. Preferably the sample heater assembly 10 includes a size of from about 1 $in^2$ to about 5 $in^2$, more preferably from about 2 $in^2$ to about 3 $in^2$, with the sample containment reservoir 14 having a receptacle or containment area of from about 0.5 $in^3$ to about 2 $in^3$, more preferably from about 1 $in^3$ to about 1.5 $in^3$.

The heating element 12 of the present invention includes any appropriate heating mechanism for effectively vaporizing the low volatility agent for detection. The heating element 12 preferably includes the Mustard Agent Heater Assembly 60 of the M256 Chemical Agent Detector Kit. As the difficulties in detection of a variety of low volatility hazards increases, thermal sources for vaporization of the chemical warfare samples may require improvement beyond that which is resident in the existing M256 Chemical Agent Detector Kit (i.e., the Mustard Agent Heater Assembly 60). This may require other thermal energy sources (with possibly more control or more energy) to increase the vapor pressure of samples placed into the present invention.

Figure 2:
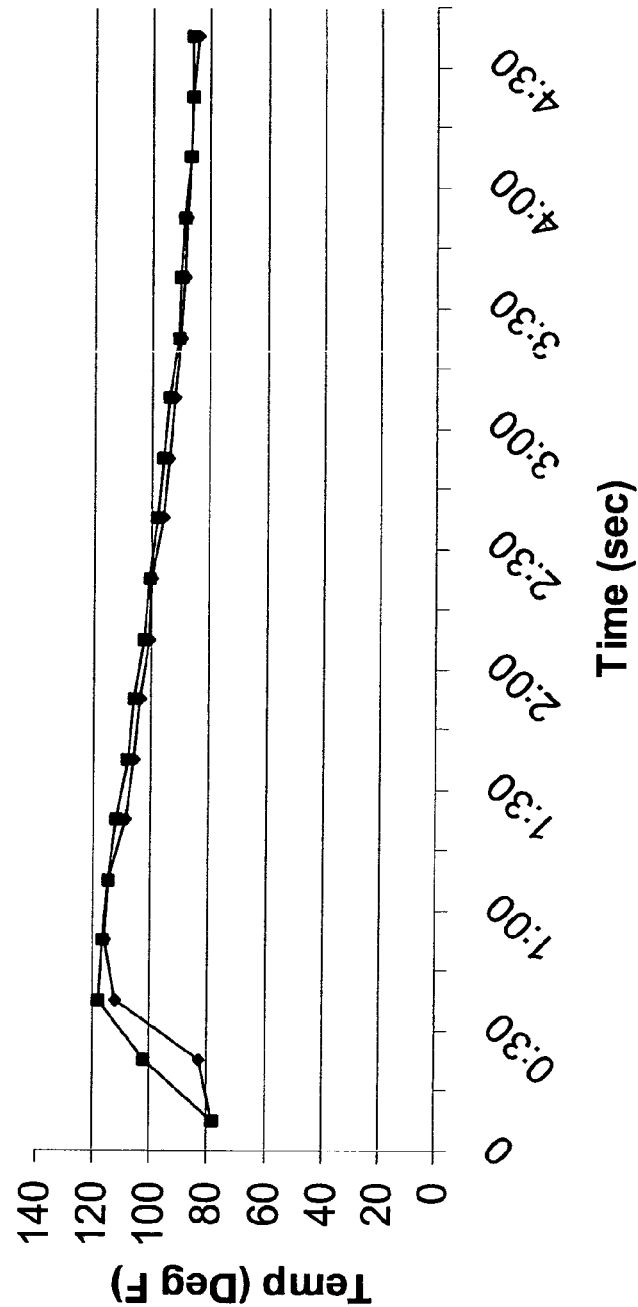
FIG. 2 is a graph of the thermal output of two ampoules, crushed simultaneously, from a Mustard Agent Heater Assembly; and, FIG. 3 illustrates the positioning of the sample heater assembly attached to the M256 Chemical Detector using a Mustard Agent Heater Assembly as a heating element.

Although use of the Mustard Agent Heater Assembly 60 is preferred, as it already exists as a component of the M256A1 Chemical Agent Detector Kit, as the direct heating source for assistance in vaporizing low vapor pressure liquids and possibly solid samples, other possible thermal vaporizing sources could be used, as well, in the present invention as the heating element 12. For example, without limitation, some samples may require specialized heating profiles distinct from the detached Mustard Agent Heater Assembly 60, including the possible requirement for additional thermal energy, such as more reactants being employed, or the pyrotechnic components. Pyrotechnic components include for example without limitation, selective oxidation/reduction reactions to provide more heat energy, or to provide heat energy at a faster rate by manipulation of the reactive chemistries. Additionally, using high-density batteries, as an electrical resistive source of thermal energy, may also be applied. Preferably, any alternate thermal sources would be inexpensive, lightweight and small in size. As seen in FIG. 2, an example of a thermal energy output profile from functioning two of the Mustard Agent Heater Assembly ampoules 16 (shown in FIG. 3) at the same time is depicted. As the currently fielded M256 Kit already has a pyrotechnic heater assembly that facilitates blister agent detection, this heater assembly is detached and used as the thermal source for increasing the vapor pressure of sampled low volatility hazards in the sample containment reservoir 14. The thermal energy for enhanced vaporization of the low volatility agents can be varied by crushing, at different time intervals, one and/or two ampoules 16 from the Mustard Agent Heater Assembly 60 that constitutes part of the currently standard M256 kit, with the ampoules 16 located to the right of the mustard agent detection in the standard M256 kit. Generally, the Mustard Agent Heater Assembly 60, previously detailed, is comprised of two reactant vials containing cupric chloride (0.4 grams/ampoule) and a pad containing aluminum powder (0.285 grams/pad). When the cupric chloride ampoules are broken a chemical reaction results, producing heat. The ampoules 16 are encased in a plastic cover on front to contain the reaction components with an aluminum foil backing to assist in effective heat transfer of the chemical reaction to a chemical warfare sample.

The heating profile of the heated sample can be adjusted through changing the spacing between the sample containment reservoir 14 and the heating element 12, separately or in combination with activating two or more heating units at the same or different times, e.g., crushing the two heater ampoules 16 in the Mustard Agent Heater Assembly 60 at different times. As used herein, the term "heating profile" describes the effective heating from a variety of heating mechanisms as well as methods to apply this heating using various techniques such as time and spatial adjustments of different heating sources.

When low volatility agents are adsorbed onto material surfaces, their effective vapor pressure may be further reduced. Appropriate thermal ramping (vaporization) of the contaminated sample may be used to overcome this problem. A variety of different sample types, such as without limitation, soil, paper, liquid puddles, clothing and other like surfaces or materials, can be detected by this induced vapor pressure increase of low volatility agents, such as nerve agents. Different agents in different sample matrices may require different thermal ramping profiles in order to maintain sample integrity and sufficient mass transfer rate, with the proper amount of thermal ramping determinable by those skilled in the art through ordinary experimentation.

Referring to FIGS. 1 and 3, the sample heater assembly 10 can be inserted over the M256 detector nerve agent window 22 or other detection windows 24 (mustard or blood gas) such as those having key sampling and detection components, collectively referred to herein as detection windows 26. Different sample types and manifestations of low volatility agents may be used in conjunction with the present invention, including for example without limitation, soil, droplets, clothing, and the like, for detection using the M256 detector 40 or other appropriate detector. Preferably, the sample heater assembly 10 has a slotted connector 20 to attach to the M256 detector 40 that enables the sample heater assembly 10 to slide the sample over the appropriate M256 detector window 26. Generally, determination of whether the nerve agent window 22, or other window 24, is selected first varies depending on known intelligence of the area or capabilities, or previous detector information collected by first responders or hazardous material teams at a suspected chemical warfare (CW) site, including intelligence information such as signs and symptoms; or from other field detection systems already being deployed. Once the appropriate nerve, blood or blister agent M256 detector window 26 is selected, the sample heater assembly 10 is clipped in place over the selected M256 detection window 26.

Preferably, the sample heater assembly 10 includes a screened section 34 of the sample containment reservoir 14. More preferably, the sample heater assembly 10 is configured with a screened section of a fine mesh screen 34 that allows the low volatility agents, e.g., chemical warfare agent samples, 100 to be deposited in the sample containment reservoir 14. Examples of this fine mesh screen 34 include compositions of nylon, Teflon, polypropylene, ABS resins, etc. that are configured in a manner to allow diffusion of the heated vapors to react on the detection windows. Screens may be configured in various ways, preferably such as to contain the sample but allow vapors or gasses through an array, such as a 15 hole by 18 hole array (270 holes) at $\frac{1}{32}$ of an inch in diameter in a sample heater assembly 10 with gross dimensions of about 44 mm in length, 38 mm in width and 15 mm in height having a sample containment reservoir of about 3.75 cm$^3$. Preferably this screen 34 precludes direct contact with the detection windows 26 of the M256 detector 40. On the sample heater assembly 10, shown as directly above the sample containment reservoir 14, an attaching mechanism 18 accommodates the heating element 12, preferably the Mustard Agent Heater Assembly 60 detached from M256 detector 40. The sample heater assembly 10 preferably comprises the attaching mechanism 18 effective to place the heating element 12 above the sample containment reservoir 14, such as a slotted channel or other like mechanism for fixing the heating element 12 over the sample containment reservoir 14. In one embodiment of the slotted attaching mechanism 18, the slot provides a pinching action onto the heating element 12 to fix the heating element 12 in place. This attaching mechanism 18 on the sample heater assembly 10 allows for the insertion and positioning of the Mustard Agent Heater Assembly 60 above and apart from the sample containment reservoir 14 using the foiled backing of the Mustard Agent Heater Assembly 60 and the contents in the sample containment reservoir 14. Preferably the attaching mechanism 18 provides a means for adjusting the distance of the heater element 12 to the sample containment reservoir 14. The preferred heating element 12 comprises one or more parts of the Mustard Agent Heater Assembly 60. With the Mustard Agent Heater Assembly 60 inserted into the sample containment reservoir 14, the heater ampoules face the operator of the sample heater assembly 10 and the aluminum foil backing of the heater ampoules is adjacent to the sample containment reservoir 14. The heating element 60 may be adjusted, as desired, to various standoff distances between the Mustard Agent Heater Assembly 60 and the sample containment reservoir 14, to optimize or modify heating profiles. With adjustment of the distance between the Mustard Agent Heater Assembly 60 and the sample containment reservoir 14, thermal vaporization rates may be varied by beyond selection of the number or amount of the heat source, e.g., how many Mustard Agent Heater Assembly 60 ampoules are crushed by the operator such as crushing either one or two heater ampoules 16 of the Mustard Agent Heater Assembly 60, and the time period in between each crushing function. Additionally, in one embodiment, a heat sink may be used to modify the heating profile. When positioned in various close adjacent position distances to the sample containment reservoir 14, the Mustard Agent Heater Assembly 60 provides effective heating to vaporize low volatility agents 100 that have been placed in the sample containment reservoir 14.

The sample heater assembly 10 may further include a slotted channel 20 effective to place the sample heating assembly 10 over an appropriate detection window, with the detection window preferably part of an M256 Chemical Detector. The slotted channel 20 may include a pinching action, e.g. a decreasing width of the slot where the sample heater assembly 10 attaches firmly to the M256 Detector 40, to ensure that diffusion of the thermalized vapors from the sample containment reservoir 14 are contained locally in the small volume space between the sample containment reservoir 14 of the sample heater assembly 10 and the M256 detection window 26. Any leakage, particularly high leakage rates, out of the M256/sample heater assembly detection volume space substantially reduces the amount of vapor hazard reaching the reactants on the M256 detection window 26. As such, the effectiveness of the sample heater assembly 10 increases with increased containment of these vapors. As the heated sample is kept isolated in the sample containment reservoir/M256 detection window volume space, preferably by a clip on the sample heater assembly 10 to attach directly over the appropriate detection window 26 of the current M256 detector 40, the vapor diffusion sampling and detection normally conducted by the M256 detector 40 occurs to analyze the vapor/gas product of the low volatility hazardous materials resulting from the use of the sample heater assembly 10.

In one preferred embodiment, the sample heater assembly 10 integrates the M256 detector 40 with chemical detection paper, preferably M8 Chemical Agent Detection Paper, 32 by detecting and analyzing low volatility hazardous materials. This unique integration of these detection systems to expand their capabilities may include use of the M8 Detection Papers 32 (Paper, Chemical Agent Detector, VGH, ABC-M8) with its three dyes impregnated therein that evidence the presence of liquid hazards only. The three impregnated dyes detect G agents (nerve), liquid VX (nerve), and liquid mustard agents (H). The M8 Detection Papers 32 are used to determine the possible presence of the individual chemical warfare agents by changing specific colors due to how the different agents react with three colored dyes embedded in these papers. A preferred use of the present invention uses the M8 Papers 32 as an initial screening/sampling tool for determining the presence of liquid nerve (G or V) or mustard agents (H). After an operator or user dips a swatch of the M8 Paper 32 into a suspect liquid, any particular color change is matched to the color presented with an agent color key. Any color match indicates the possible presence of an agent hazard. After a color change from the M8 Paper 32, the user inserts the M8 Paper 32 into the sample heater assembly 10 which is then clamped in place to the appropriate detection window 26 of the M256 detector 40 to further analyze the suspect agent hazard. In this embodiment, preferably a color-coded legend is added to the M256 detection windows 26, allowing the operator to select, or confirm, the appropriate detection window 26 with the color code. More preferably, any color coding of the M256 detection window 26 is adjacent to the individual windows of the M256 detector 40. For example, color coding of the detection windows using colored block legends, e.g., if the M8 paper 32 turns gold or green then as per the color legend the sample heater assembly 10 would be placed over that detection window, e.g., a starred window, and then the appropriately colored M8 paper 32 would be inserted for desorption to a vapor. If the M8 paper 32 turns red, then the sample heater assembly 10 would be placed over the blister agent detection window, e.g., a square window, and desorbed as stated above.

The integration of the previously independent M256 Chemical Agent Detector 40 and the M8 Detector Papers 32 is operationally advantageous. The M8 Papers 32, when operationally used in conjunction with the M256 and sample heater assembly 10, provides the user with presumptive chemical hazard detection, i.e., low vapor pressure liquid sampling. It also provides a method to sample and confirm M8 Paper 32 presumptive detection of low vapor pressure hazards by rapid, logical calorimetric analysis using the attributes of the M256/sample heater assembly integration.

Although the sample heater assembly 10 may be considered a low cost and expendable item, sample heater assembly 10 may be effectively field decontaminated for subsequent reuse. As an inexpensive, small and lightweight device, the sample heater assembly 10 can be included and packaged in the current M256 field containers. With the Mustard Agent Heater Assembly 60 already in use and attached to the current M256 kit, there exists an immediate heating capability in the fielded units. However, because the individual heaters in the Mustard Agent Heater Assembly 60 are small, additional heaters may be added to a modified M256 kit.

When detecting low volatility agents 100, one or more low volatility agents 100 are placed into the sample containment reservoir 14 of the sample heater assembly 10 and the sample containment reservoir 14 is heated to effectively vaporize the low volatility agents 100 for detection by an appropriate detection device. Preferably, the low volatility agents 100 placed into the sample containment reservoir 14 have been detected as chemical warfare agent with chemical detection paper, such as M8 Detection Paper, 32 with the M8 Detection Paper 32 (with detected absorbed chemical warfare) inserted into the sample containment reservoir 14. In operation, the integrated sample heater assembly 10 and M256 detector 40, functioning as a combined system, provide for a tight fitting, small volume sample containment reservoir 14 which precludes extraneous diffusion of the low vapor pressure sample vapors outside the sample containment reservoir 14 area. This enhancement of field operated detection devices, particularly currently used detection devices significantly increases the usefulness of these devices in detection of low volatility hazards. The method of the present invention results in a detected chemical warfare agent product.

The sample heater assembly 10 of the present invention may be incorporated into a kit, such as an M256 Chemical Detection kit.

EXAMPLE 1

An M256 detector kit sample heater assembly for the M256 Detector Kit was designed and fabricated. The sample heater assembly was constructed of a polypropylene material, with the dimensions of 0.269 cubic inches internal volume, 0.095 inch slotted channel for attaching the M256 detector, and 0.075 slot for the attaching mechanism for attaching the heating element. The sample heater assembly was 1.750 inches in length, 1.619 inches in width and 0.710 inches high. The screen within the sample heater assembly had 293 holes at 0.032 diameter each (293×__.032).

EXAMPLE 2

A theoretical assessment of the thermal desorption and mass transfer kinetics were calculated for the sample heater assembly configuration of Example 1 using the low volatility nerve agent VX as the target hazardous liquid. Given the detection limit of the M256 detector as 0.005 mg/m$^3$, and assuming the mustard agent heater assembly achieve a temperature over 100° C. for 5 minutes when both ampoules are broke, the present invention was determined to detect low volatility agents like VX (assuming typical battlefield contamination densities) in less than one second. This results in the heated detection probe and sampling vessel for the modified 256 Kit and eel enzyme detection technology as having the potential to detect VX vapors when operated at an elevated temperature of approximately 100° F.

The present invention provides an enhanced Improved Chemical Agent Monitor (ICAM) or M256 Chemical Agent Detection System for general-purpose low vapor pressure sampling and detection in field environments. The sample heater assembly of the present invention is simple to use, disposable, and versatile enough to detect a variety of field samples on site that have either low volatilities or adsorbed in an environmental sample matrix that precludes adequate vaporization. Additionally, toxic industrial hazards may be detected using the sample heater assembly in combination with appropriately configured detection kits, permitting detection of low volatility hazards in the commercial and/or industrial area.

The foregoing summary, description, and examples of the present invention are not intended to be limiting, but are only exemplary of the inventive features which are defined in the claims. Alternative materials and configurations as those described herein for the present invention may be used.

What is claimed is:

1. A sample heater assembly for use with a chemical agent detector, comprising:
   a sample containment reservoir having means for attaching to said chemical agent detector, said sample containment reservoir also having means for attaching a heating element to said sample containment reservoir; wherein said means for attaching said heating element to said sample containment reservoir further comprises a means for adjusting the distance between the heating element and the sample containment reservoir; and wherein said heating element is attached to said sample containment reservoir so that low volatility agents contained in said reservoir are effectively vaporized and detected by said detector.

2. The sample beater assembly of claim 1, wherein said chemical agent detector comprises the M256 Chemical Agent Detector.

3. The sample heater assembly of claim 2, wherein said means for attaching said sample containment reservoir to said detector comprises a slotted channel.

4. The sample heater assembly of claim 2, wherein said means for attaching said heating element to said sample containment reservoir comprises a slotted channel.

5. The sample heater assembly of claim 4, wherein said slotted channel is effective for positioning said sample containment reservoir over a detection window in said M256 Detector.

6. The sample heater assembly of claim 4, wherein said slotted channel positions said heating element above said reservoir.

7. The sample heater assembly of claim 2, wherein said heating element comprises a Mustard Agent Heating Assembly.

8. The sample heater assembly of claim 1, wherein said sample containment reservoir includes a screened section to permit vaporized agents to pass therethrough.

9. The sample heater assembly of claim 1, wherein said heating element comprises a battery driven electrical resistance heater.

10. The sample heater assembly of claim 1, wherein said heating element comprises a chemical reaction heater.

11. The sample heater assembly of claim 1, wherein said heating element comprises pyrotechnic components for heat generation.

12. The sample heater assembly of claim 1, wherein said low volatility agents comprise one or more chemical warfare agents.

13. The sample heater assembly of claim 12, wherein said one or more chemical warfare agents are selected from the group consisting of blister agents, blood agents, and nerve agents.

14. The sample heater assembly of claim 13, wherein said nerve agent comprises VX.

15. A method for detecting low volatility agents, comprising the steps of:
   providing a sample containment reservoir having means for attaching to a chemical agent detector, said sample containment reservoir also having means for attaching a heating element to said sample containment reservoir; wherein said means for attaching said heating element to said sample containment reservoir further comprises a means for adjusting the distance between the heating element and the sample containment reservoir;
   attaching said sample containment reservoir to said chemical agent detector;
   placing one or more low volatility agents into said sample containment reservoir;
   attaching a heating element to said sample containment reservoir; and
   heating the sample containment reservoir effectively to vaporize the low volatility agents for detection by said chemical agent detector.

16. The method of claim 15, wherein said heating element comprises a Mustard Agent Heater Assembly.

17. The method of claim 15, wherein said one or more low volatility agents comprises chemical warfare agents.

18. The method of claim 15, wherein the step of placing one or more low volatility agents into said sample containment reservoir further comprises the steps of absorbing a low volatility agent with M8 Detection Paper and inserting the M8 Detection Paper having absorbed low volatility agent into said sample containment reservoir.

* * * * *